United States Patent
Sharma et al.

(10) Patent No.: US 9,463,196 B2
(45) Date of Patent: *Oct. 11, 2016

(54) PHARMACEUTICAL COMPOSITION OF DOXYCYCLINE WITH REDUCED FOOD EFFECT

(71) Applicant: SUN PHARMACEUTICAL INDUSTRIES LIMITED, Mumbai, Maharashtra (IN)

(72) Inventors: Ravish Kumar Sharma, Khargone (IN); Pulak Kumar Metia, Howrah (IN); Ravinder Singh, Gurgaon (IN); Rajesh Srikrishan Shear, Gurgaon (IN); Anuj Kumar Fanda, Ghaziabad (IN); Satish Kumar Jain, Bilaspur (IN); Romi Barat Singh, Varanasi (IN); Swarna Pappu, Monroe, NJ (US); Prabhakar Konatham, Princeton, NJ (US); Pruthvipathy Katikaneni, Parsippany, NJ (US); Dileep Jami, Srikakulam (IN)

(73) Assignee: SUN PHARMACEUTICAL INDUSTRIES LIMITED, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 14/821,263

(22) Filed: Aug. 7, 2015

(65) Prior Publication Data
US 2016/0008379 A1    Jan. 14, 2016

Related U.S. Application Data

(63) Continuation-in-part of application No. 14/326,949, filed on Jul. 9, 2014, now Pat. No. 9,132,092.

(30) Foreign Application Priority Data

Mar. 23, 2015   (IN) .............................. 791/DEL/2015

(51) Int. Cl.
| A61K 31/65 | (2006.01) |
| A61K 9/20 | (2006.01) |
| A61K 9/24 | (2006.01) |
| A61K 9/16 | (2006.01) |

(52) U.S. Cl.
CPC ............... *A61K 31/65* (2013.01); *A61K 9/209* (2013.01); *A61K 9/2027* (2013.01); *A61K 9/2054* (2013.01); *A61K 9/2081* (2013.01); *A61K 9/1676* (2013.01)

(58) Field of Classification Search
CPC ...................................... A61K 9/209
USPC ........................................ 514/152; 424/465
See application file for complete search history.

(56) References Cited

U.S. PATENT DOCUMENTS 7,749,532 B2    7/2010   Chang et al. ................. 424/458
9,132,092 B1 *  9/2015   Sharma ................ A61K 9/2054

OTHER PUBLICATIONS

Agwuh et al., "Pharmacokinetics and pharmacodynamics of the tetracyclines including glycylcyclines," *Journal of Antimicrobial Chemotherapy*, 58(2):256-265 (2006).

* cited by examiner

*Primary Examiner* — Raymond Henley, III

(57) ABSTRACT

The present invention relates to a once daily tablet comprising doxycycline at sub-antibiotic dose and one or more pharmaceutically acceptable excipients, wherein the tablet exhibits a reduced food effect. The invention further provides a method of treatment of rosacea by administering to a person in need thereof the doxycycline tablet with or without food. A process of preparing the tablet is also provided.

17 Claims, No Drawings

PHARMACEUTICAL COMPOSITION OF DOXYCYCLINE WITH REDUCED FOOD EFFECT

FIELD OF THE INVENTION

The present invention relates to a once daily tablet comprising doxycycline at sub-antibiotic dose and one or more pharmaceutically acceptable excipients, wherein the tablet exhibits a reduced food effect. The invention further provides a method of treatment of rosacea by administering to a person in need thereof the doxycycline tablet disclosed herein with or without food. A process of preparing the tablet is also provided.

BACKGROUND OF THE INVENTION

Food effect refers to food-drug interactions which lead to either a decrease or an increase of the extent of drug absorption. The commercially available capsules of doxycycline (Oracea® 40 mg capsules) for the treatment of inflammatory lesions (papules and pustules) of rosacea is a combination of immediate release (30 mg) and delayed release (10 mg) components. As per the prescribing information, the capsules have significant food effect and thus are recommended to be taken on an empty stomach, preferably at least one hour prior to or two hours after meals. The $C_{max}$ and $AUC_{0-t}$ of Oracea® decrease by 45% and 22% respectively when taken along with food.

Therefore, there exists a need for a pharmaceutical composition of doxycycline which is capable of reducing the food effect of doxycycline. The present inventors have developed a pharmaceutical composition of doxycycline in the form of a tablet with reduced food effect, which would enable the patient to take the drug without regard to meals, thereby improving patient convenience and compliance.

SUMMARY OF THE INVENTION

The present invention relates to a once daily tablet comprising doxycycline at sub-antibiotic dose and one or more pharmaceutically acceptable excipients, wherein the tablet exhibits a reduced food effect. The invention further provides a method of treatment of rosacea by administering to a person in need thereof the doxycycline tablet with or without food. A process of preparing the tablet is also provided. It is possible to reduce the dose if food effect is minimized, as the same therapeutic levels may be achieved with a lesser amount of doxycycline. Accordingly, the present invention also provides a low dose once daily tablet comprising doxycycline at sub-antibiotic dose and one or more pharmaceutically acceptable excipients, wherein the tablet exhibits a reduced food effect.

DETAILED DESCRIPTION OF THE INVENTION

A first aspect of the present invention provides a once daily tablet comprising doxycycline and one or more pharmaceutically acceptable excipients, wherein the tablet exhibits a reduced food effect such that the food effect on $C_{max}$ is less than 40%, as compared to when the tablet is administered in a fasted state.

According to one embodiment of the above aspect, the once daily tablet comprising doxycycline and one or more pharmaceutically acceptable excipients, wherein the tablet exhibits a reduced food effect such that the food effect on $C_{max}$ is less than 20%, as compared to when the tablet is administered in a fasted state.

According to another embodiment of the above aspect, the once daily tablet comprises (i) 50% to 99% of doxycycline and one or more pharmaceutically acceptable excipients as an immediate-release portion; and (ii) 1% to 50% of doxycycline, a controlled-release polymer, and one or more pharmaceutically acceptable excipients as a controlled-release portion.

According to the above embodiments, the immediate-release portion contains 85% of doxycycline and the controlled-release portion contains 15% of doxycycline.

According to the above embodiment, the immediate-release portion contains 34 mg of doxycycline and the controlled-release portion contains 6 mg of doxycycline.

According to the above embodiment, the immediate-release portion contains 75% of doxycycline and the controlled-release portion contains 25% of doxycycline.

According to the above embodiment, the immediate-release portion contains 30 mg of doxycycline and the controlled-release portion contains 10 mg of doxycycline.

According to the above embodiment, the immediate-release portion contains 66% of doxycycline and the controlled-release portion contains 34% of doxycycline.

According to the above embodiment, the immediate-release portion contains 26.4 mg of doxycycline and the controlled-release portion contains 13.6 mg of doxycycline.

According to the above embodiment, the immediate-release portion contains 65% of doxycycline and the controlled-release portion contains 35% of doxycycline.

According to the above embodiment, the immediate-release portion contains 26 mg of doxycycline and the controlled-release portion contains 14 mg of doxycycline.

According to the above embodiment, the immediate-release portion contains 60% of doxycycline and the controlled-release portion contains 40% of doxycycline.

According to the above embodiment, the immediate-release portion contains 24 mg of doxycycline and the controlled-release portion contains 16 mg of doxycycline.

A second aspect of the present invention provides a once daily tablet comprising doxycycline and one or more pharmaceutically acceptable excipients, wherein the tablet exhibits a reduced food effect such that the food effect on $AUC_{0-t}$ is less than 20%, compared to when the tablet is administered in a fasted state.

According to an embodiment of the above aspect, the once daily tablet comprises (i) 50% to 99% of doxycycline and one or more pharmaceutically acceptable excipients as an immediate-release portion; and (ii) 1% to 50% of doxycycline, a controlled-release polymer, and one or more pharmaceutically acceptable excipients as a controlled-release portion.

According to the above embodiments, the immediate-release portion contains 85% of doxycycline and the controlled-release portion contains 15% of doxycycline.

According to the above embodiment, the immediate-release portion contains 34 mg of doxycycline and the controlled-release portion contains 6 mg of doxycycline.

According to the above embodiment, the immediate-release portion contains 75% of doxycycline and the controlled-release portion contains 25% of doxycycline.

According to the above embodiment, the immediate-release portion contains 30 mg of doxycycline and the controlled-release portion contains 10 mg of doxycycline.

According to the above embodiment, the immediate-release portion contains 66% of doxycycline and the controlled-release portion contains 34% of doxycycline.

According to the above embodiment, the immediate-release portion contains 26.4 mg of doxycycline and the controlled-release portion contains 13.6 mg of doxycycline.

According to the above embodiment, the immediate-release portion contains 65% of doxycycline and the controlled-release portion contains 35% of doxycycline.

According to the above embodiment, the immediate-release portion contains 26 mg of doxycycline and the controlled-release portion contains 14 mg of doxycycline.

According to the above embodiment, the immediate-release portion contains 60% of doxycycline and the controlled-release portion contains 40% of doxycycline.

According to the above embodiment, the immediate-release portion contains 24 mg of doxycycline and the controlled-release portion contains 16 mg of doxycycline.

A third aspect of the present invention provides a low dose once daily tablet comprising doxycycline at a sub-antibiotic dose and one or more pharmaceutically acceptable excipients, wherein the tablet exhibits a reduced food effect.

According to an embodiment of this aspect, the sub-antibiotic dose of doxycycline is in the range of 24 mg to 36 mg.

According to another embodiment of the above aspect, the sub-antibiotic dose of doxycycline is in the range of 30 mg to 36 mg.

According to another embodiment of the above aspect, the sub-antibiotic dose of doxycycline is in the range of 32 mg to 36 mg.

According to another embodiment of the above aspect, the sub-antibiotic dose of doxycycline is 24 mg.

According to another embodiment of the above aspect, the sub-antibiotic dose of doxycycline is 26 mg.

According to another embodiment of the above aspect, the sub-antibiotic dose of doxycycline is 28 mg.

According to another embodiment of the above aspect, the sub-antibiotic dose of doxycycline is 30 mg.

According to another embodiment of the above aspect, the sub-antibiotic dose of doxycycline is 32 mg.

According to another embodiment of the above aspect, the sub-antibiotic dose of doxycycline is 34 mg.

According to another embodiment of the above aspect, the sub-antibiotic dose of doxycycline is 36 mg.

According to another embodiment of the above aspect, the dose of doxycycline is reduced by 10% in comparison to the marketed Oracea® capsules containing 40 mg of doxycycline.

According to another embodiment of the above aspect, the dose of doxycycline is reduced by 15% in comparison to the marketed Oracea® capsules containing 40 mg of doxycycline.

According to another embodiment of the above aspect, the dose of doxycycline is reduced by 20% in comparison to the marketed Oracea® capsules containing 40 mg of doxycycline.

According to another embodiment of the above aspect, the dose of doxycycline is reduced by 30% in comparison to the marketed Oracea® capsules containing 40 mg of doxycycline.

According to another embodiment of the above aspect, the dose of doxycycline is reduced by 40% in comparison to the marketed Oracea® capsules containing 40 mg of doxycycline.

According to another embodiment, the food effect on $C_{max}$ is less than 40%, compared to when the tablet is administered in a fasted state.

According to another embodiment, the food effect on $AUC_{0-t}$ is less than 20%, compared to when the tablet is administered in a fasted state.

According to another embodiment of the above aspect, the low dose once daily tablet comprises (i) 50% to 99% of doxycycline and one or more pharmaceutically acceptable excipients as an immediate-release portion; and (ii) 1% to 50% of doxycycline, a controlled-release polymer, and one or more pharmaceutically acceptable excipients as a controlled-release portion, wherein the once daily tablet provides a total daily dosage of 24 mg to 36 mg doxycycline when administered once daily.

According to the above embodiments, the immediate-release portion contains 94% of doxycycline and the controlled-release portion contains 6% of doxycycline.

According to the above embodiments, the immediate-release portion contains 93% of doxycycline and the controlled-release portion contains 7% of doxycycline.

According to the above embodiments, the immediate-release portion contains 89% of doxycycline and the controlled-release portion contains 11% of doxycycline.

According to the above embodiments, the immediate-release portion contains 88% of doxycycline and the controlled-release portion contains 12% of doxycycline.

According to the above embodiments, the immediate-release portion contains 87% of doxycycline and the controlled-release portion contains 13% of doxycycline.

According to the above embodiments, the immediate-release portion contains 85% of doxycycline and the controlled-release portion contains 15% of doxycycline.

According to the above embodiments, the immediate-release portion contains 83% of doxycycline and the controlled-release portion contains 17% of doxycycline.

According to the above embodiments, the immediate-release portion contains 75% of doxycycline and the controlled-release portion contains 25% of doxycycline.

According to the above embodiments, the immediate-release portion contains 65% of doxycycline and the controlled-release portion contains 35% of doxycycline.

According to the above embodiments, the immediate-release portion contains 66% of doxycycline and the controlled-release portion contains 34% of doxycycline.

According to the above embodiments, the immediate-release portion contains 60% of doxycycline and the controlled-release portion contains 40% of doxycycline.

A fourth aspect of the present invention provides a low dose once daily tablet comprising doxycycline at a sub-antibiotic dose and one or more pharmaceutically acceptable excipients, wherein the tablet exhibits a reduced food effect, and wherein the tablet comprises only an immediate-release portion.

According to one embodiment of the above aspect, the immediate-release portion comprises from 24 mg to 36 mg of doxycycline.

According to another embodiment of the above aspect, the immediate-release portion comprises 24 mg of doxycycline.

According to another embodiment of the above aspect, the immediate-release portion comprises 26 mg of doxycycline.

According to another embodiment of the above aspect, the immediate-release portion comprises 28 mg of doxycycline.

According to another embodiment of the above aspect, the immediate-release portion comprises 30 mg of doxycycline.

According to another embodiment of the above aspect, the immediate-release portion comprises 32 mg of doxycycline.

According to another embodiment of the above aspect, the immediate-release portion comprises 34 mg of doxycycline.

According to another embodiment of the above aspect, the immediate-release portion comprises 36 mg of doxycycline.

A fifth aspect of the present invention provides a low dose once daily tablet comprising doxycycline at a sub-antibiotic dose and one or more pharmaceutically acceptable excipients, wherein the tablet exhibits a reduced food effect, and wherein the tablet comprises only a controlled-release portion.

According to one embodiment of this aspect, the controlled-release portion may comprise from 24 mg to 36 mg of doxycycline.

According to another embodiment of the above aspect, the controlled-release portion comprises 24 mg of doxycycline.

According to another embodiment of the above aspect, the controlled-release portion comprises 26 mg of doxycycline.

According to another embodiment of the above aspect, the controlled-release portion comprises 28 mg of doxycycline.

According to another embodiment of the above aspect, the controlled-release portion comprises 30 mg of doxycycline.

According to another embodiment of the above aspect, the controlled-release portion comprises 32 mg of doxycycline.

According to another embodiment of the above aspect, the controlled-release portion comprises 34 mg of doxycycline.

According to another embodiment of the above aspect, the controlled-release portion comprises 36 mg of doxycycline.

A sixth aspect of the present invention provides a process for the preparation of a once daily tablet comprising doxycycline at a sub-antibiotic dose and one or more pharmaceutically acceptable excipients, wherein the tablet exhibits a reduced food effect, and wherein the process comprises:
  a) preparing an immediate-release portion comprising doxycycline and one or more pharmaceutically acceptable excipients;
  b) preparing a controlled-release portion comprising doxycycline, a controlled release polymer, and one or more pharmaceutically acceptable excipients; and
  c) formulating the immediate-release portion and the controlled-release portion into a tablet.

According to one embodiment of the above aspect, the tablet is a bilayered tablet.

According to another embodiment of the above aspect, the tablet comprises only an immediate-release portion.

According to another embodiment of the above aspect, the tablet comprises only a controlled-release portion.

A seventh aspect of the present invention provides a method of treating rosacea by administering to a person in need thereof a once daily tablet comprising doxycycline and one or more pharmaceutically acceptable excipients, wherein the tablet exhibits a reduced food effect such that the food effect on $C_{max}$ is less than 40%, compared to when the tablet is administered in a fasted state.

A eighth aspect of the present invention provides a method of treating rosacea by administering to a person in need thereof a once daily tablet comprising doxycycline and one or more pharmaceutically acceptable excipients, wherein the tablet exhibits a reduced food effect such that the food effect on $AUC_{0-t}$ is less than 20%, compared to when the tablet is administered in a fasted state.

A ninth aspect of the present invention provides a method of treating rosacea by administering to a person in need thereof a low dose once daily tablet comprising (i) 50% to 99% of doxycycline and one or more pharmaceutically acceptable excipients as an immediate-release portion; and (ii) 1% to 50% of doxycycline, a controlled-release polymer, and one or more pharmaceutically acceptable excipients as a controlled-release portion, wherein the once daily tablet provides a total daily dosage of 24 mg to 36 mg of doxycycline when administered once daily.

The term "doxycycline," as used herein, includes doxycycline base and its pharmaceutically acceptable salts, hydrates, solvates, esters, or prodrugs. Preferably, doxycycline is used as its hyclate salt, which is doxycycline hydrochloride hemiethanolate hemihydrate.

The term "bioavailability," as used herein, refers to the fraction of a drug that reaches systemic circulation after oral administration. Parameters used in the measurement of bioavailability are $C_{max}$ (maximum plasma concentration), $AUC_{0-t}$ (area under the curve), and $T_{max}$ (time to reach maximum plasma concentration), which are well known in the art.

The term "food effect," as used herein, refers to relative differences in $AUC_{0-t}$ and $C_{max}$ of a drug when it is administered in a fed state as compared to when it is administered in a fasted state.

The term "reduced food effect," as used herein, refers to a state wherein food decreases $C_{max}$ and $AUC_{0-t}$ by less than 40% and 20%, respectively, in a fed state when compared to $C_{max}$ and $AUC_{0-t}$ in a fasted state. Doxycycline has an absorption window in the upper part of the gastrointestinal tract. In the present invention, reduced food effect has been achieved with a tablet dosage form. The tablet has increased gastric residence time, which exposes the drug to the site of absorption for a longer duration of time.

The term "fasted state," as used herein, refers to a gap of at least two hours between the meal and administration of the tablet.

The term "fed state," as used herein, refers to administration from about 1 hour before a meal to about 1 hour after a meal.

The term "immediate release portion," as used herein, refers to that portion of the dosage form which releases the drug immediately upon contact with gastric juices.

The term "controlled-release portion," as used herein, refers to that portion of the dosage form which contains a controlled-release polymer and releases the drug in a controlled manner over a period of time. Controlled-release can also be referred to as sustained release (SR), prolonged release (PR), or extended release (ER).

Suitable controlled-release polymers are selected from the group comprising hydroxypropylmethyl cellulose, hydroxypropyl cellulose, methyl cellulose, sodiumcarboxymethyl cellulose, hydroxyethyl cellulose, carboxymethyl ethyl cellulose, ethyl cellulose, cellulose acetate, cellulose nitrate, polymethacrylic copolymer, poloxamers, polyoxyethylene stearate, polyvinyl pyrrolidone, polyvinylpyrrolidone-polyvinylacetate copolymer, polyvinyl alcohol, polyethylene oxide, gums (e.g., xanthan gum, tragacanth gum, gum karaya, guar gum, acacia gum, and locust bean gum), fatty acids, fatty acid esters, alkyl alcohols, wax, shellac, and mixtures thereof.

The term "pharmaceutically acceptable excipients," as used herein, includes any physiologically inert additives that are routinely used in pharmaceutical compositions. Pharmaceutically acceptable excipients are selected from the group comprising binders, diluents, disintegrants, lubricants/glidants/antiadherants, acidifying agents, and mixtures thereof.

Examples of binders include povidone, copovidone, polyvinyl pyrrolidone, hydroxypropylmethyl cellulose, hydroxypropyl cellulose, hydroxyethyl cellulose, methyl cellulose, ethyl cellulose, xanthan gum, gum acacia, gum arabic, tragacanth, sorbitol, dextrose, sucrose, mannitol, gelatin, pullulan, sodium alginate, calcium alginate, ammonium calcium alginate, propylene glycol, polyvinyl alcohol, corn syrup, methacrylates, carboxyvinyl polymers, e.g., carbomers, and mixtures thereof.

Examples of diluents include microcrystalline cellulose, powdered cellulose, dibasic calcium phosphate, tribasic calcium phosphate, calcium sulfate, calcium carbonate, lactose monohydrate, lactose anhydrous, sucrose, sorbitol, xylitol, erythritol, kaolin, calcium silicate, maltodextrin, starch, modified starch (e.g., pregelatinized starch, maize starch, and corn starch), and mixtures thereof.

Examples of disintegrants include hydroxypropyl cellulose (L-HPC), crospovidone, croscarmellose sodium, carboxymethyl cellulose sodium, carboxymethyl cellulose calcium, sodium starch glycolate, gums, alginic acid or alginates, starch, corn starch, modified starch, carboxymethyl starch, polyacrylates, and mixtures thereof.

Examples of lubricants/glidants/antiadherents include magnesium stearate, hydrogenated vegetable oil, glyceryl behenate, glyceryl monostearate, stearic acid, sodium stearyl fumarate, calcium stearate, zinc stearate, aluminum silicate, talc, colloidal silicon dioxide, sucrose esters of fatty acids, waxes, silica gel, and mixtures thereof.

Acidifying agents are pH modifiers which provide an acidic environment required for stability of the drug. Examples of acidifying agents include citric acid, tartaric acid, adipic acid, fumaric acid, malic acid, acetic acid, lactic acid, hydrochloric acid, phosphoric acid, and mixtures thereof.

Various solvents that may be employed during the preparation of the pharmaceutical composition of the present invention are selected from the group comprising methyl alcohol, ethyl alcohol, isopropyl alcohol, n-butyl alcohol, acetone, acetonitrile, chloroform, methylene chloride, water, and mixtures thereof.

The pharmaceutical composition of the present invention may be prepared by any of the well-known processes including wet granulation, dry granulation, direct compression, top spray granulation, and drug layering.

The pharmaceutical composition of the present invention is in the form of a tablet. The tablet may be single layered, bilayered, or an inlay tablet. The tablet may be further coated with a film coating prepared by using a film-forming polymer and one or more pharmaceutically acceptable excipients. The pharmaceutically acceptable excipients may be plasticizers, opacifiers, coloring agents, and mixtures thereof.

Examples of film-forming polymers include hydroxypropylmethyl cellulose, ethyl cellulose, methyl cellulose, hydroxyethyl cellulose, hydroxypropyl cellulose, sodium carboxymethyl cellulose, cellulose acetate, hydroxypropylmethyl cellulose phthalate, cellulose acetate trimellitate, methacrylic acid copolymers (e.g., Eudragit®), polyvinyl pyrrolidone, polyvinyl alcohol, polyethylene glycol, and mixtures thereof. A preferred film-forming polymer is hydroxypropylmethyl cellulose. Other suitable film-forming polymers which are known in the art may also be used. Alternatively, commercially available coating compositions comprising film-forming polymers marketed under various trade names, such as Opadry® and Opaglos®, may also be used.

Examples of plasticizers include propylene glycol, triethyl citrate, tributyl citrate, dibutyl sebacate, acetyl tributyl citrate, glyceryl monostearate, triacetin, polyethylene glycol, diethyl phthalate, acetylated monoglycerides, diacetylated monoglycerides, cetyl alcohol, and mixtures thereof.

Examples of opacifiers include titanium dioxide, manganese dioxide, iron oxide, silicon dioxide, and mixtures thereof.

The coloring agents may be selected from FDA approved colorants such as iron oxide, lake of tartrazine, allura red, titanium dioxide, and mixtures thereof.

The coating may be carried out by using any conventional coating techniques known in the art, such as spray coating in a conventional coating pan or fluidized bed processor, or dip coating.

For the terms "for example" and "such as," and grammatical equivalences thereof, the phrase "and without limitation" is understood to follow unless explicitly stated otherwise. As used herein, the term "about" is meant to account for variations due to experimental error. All measurements reported herein are understood to be modified by the term "about," whether or not the term is explicitly used, unless explicitly stated otherwise. As used herein, the singular forms "a," "an," and "the" include plural referents unless the context clearly dictates otherwise.

The following examples illustrate the present invention but are not to be construed as limiting the scope of the invention.

EXAMPLES

Example 1

| Ingredients | Quantity (% w/w) |
|---|---|
| Immediate Release Layer | |
| Doxycycline hyclate equivalent to doxycycline base 24 mg | 9.60 |
| Microcrystalline cellulose (Avicel ® PH 102) | 33.50 |
| Crospovidone | 2.91 |
| Polyvinyl pyrrolidone | 1.70 |
| Colloidal silicon dioxide | 0.24 |
| Iron oxide yellow | 0.49 |
| Magnesium stearate | 0.10 |
| Controlled Release Layer | |
| Doxycycline hyclate equivalent to doxycycline base 16 mg | 6.40 |
| Microcrystalline cellulose (Avicel ® PH 102) | 16.38 |
| Microcrystalline cellulose (Avicel ® PH 200) | 13.88 |
| Hydroxypropylmethyl cellulose (Methocel ® K4M Premium CR) | 4.85 |
| Hydroxypropylmethyl cellulose (Methocel ® K100 Premium LV) | 4.85 |
| Polyvinyl pyrrolidone | 1.46 |
| Colloidal silicon dioxide | 0.24 |
| Magnesium stearate | 0.49 |
| Coating | |
| Opadry ® | 2.91 |
| Purified water | q.s. |

Manufacturing Process
Immediate Release Portion
1. Doxycycline hyclate, Avicel® PH 102, iron oxide yellow, crospovidone, polyvinyl pyrrolidone, colloidal silicon dioxide, and magnesium stearate were mixed to form a blend.

Controlled Release Portion
2. Doxycycline hyclate, Avicel® PH 102, Avicel® PH 200, Methocel® K4M, Methocel® K100, polyvinyl pyrrolidone, and colloidal silicon dioxide were mixed to form a blend.
3. The blend of step 2 was lubricated with magnesium stearate to form a final blend.

Compression
4. The blend of step 1 was compressed, followed by compression of the final blend of step 3 to form bilayer tablets.
5. Opadry® was dispersed in purified water to form a dispersion.
6. The tablets of step 4 were coated with the Opadry® dispersion of step 5.

Example 2

| Ingredients | Quantity (% w/w) |
|---|---|
| Immediate Release Layer | |
| Doxycycline hyclate equivalent to doxycycline base 26.4 mg | 10.56 |
| Microcrystalline cellulose (Avicel ® PH 102) | 32.54 |
| Crospovidone | 2.91 |
| Polyvinyl pyrrolidone | 1.70 |
| Colloidal silicon dioxide | 0.24 |
| Iron oxide yellow | 0.49 |
| Magnesium stearate | 0.10 |
| Controlled Release Layer | |
| Doxycycline hyclate equivalent to doxycycline base 13.6 mg | 5.44 |
| Microcrystalline cellulose (Avicel ® PH 102) | 17.34 |
| Microcrystalline cellulose (Avicel ® PH 200) | 13.87 |
| Hydroxypropylmethyl cellulose (Methocel ® K4M Premium CR) | 2.43 |
| Hydroxypropylmethyl cellulose (Methocel ® K100 Premium LV) | 7.28 |
| Polyvinyl pyrrolidone | 1.46 |
| Colloidal silicon dioxide | 0.24 |
| Magnesium stearate | 0.49 |
| Coating | |
| Opadry ® | 2.91 |
| Purified water | q.s. |

Manufacturing Process
Immediate Release Portion
1. Doxycycline hyclate, Avicel® PH 102, iron oxide yellow, crospovidone, polyvinyl pyrrolidone, colloidal silicon dioxide, and magnesium stearate were mixed to form a blend.

Controlled Release Portion
2. Doxycycline hyclate, Avicel® PH102, Avicel® PH 200, Methocel® K4M, Methocel® K100, polyvinyl pyrrolidone, and colloidal silicon dioxide were mixed to form a blend.
3. The blend of step 2 was lubricated with magnesium stearate to form a final blend.

Compression
4. The blend of step 1 was compressed, followed by compression of the final blend of step 3 to form bilayer tablets.
5. Opadry® was dispersed in purified water to form a dispersion.
6. The tablets of step 4 were coated with the Opadry® dispersion of step 5.

Example 3

| Ingredients | Quantity (% w/w) |
|---|---|
| Immediate Release Layer | |
| Doxycycline hyclate equivalent to doxycycline base 34 mg | 13.61 |
| Microcrystalline cellulose (Avicel ® PH 102) | 29.50 |
| Crospovidone | 2.91 |
| Polyvinyl pyrrolidone | 1.70 |
| Colloidal silicon dioxide | 0.24 |
| Iron oxide yellow | 0.49 |
| Magnesium Stearate | 0.10 |
| Controlled Release Layer | |
| Doxycycline hyclate equivalent to doxycycline base 6 mg | 2.40 |
| Microcrystalline cellulose (Avicel ® PH 102) | 17.95 |
| Microcrystalline cellulose (Avicel ® PH 200) | 13.87 |
| Hydroxypropylmethyl cellulose (Methocel ® K100 Premium LV) | 12.14 |
| Polyvinyl pyrrolidone | 1.46 |
| Colloidal silicon dioxide | 0.24 |
| Magnesium stearate | 0.48 |
| Coating | |
| Opadry ® | 2.91 |
| Purified water | q.s. |

Manufacturing Process
Immediate Release Portion
1. Doxycycline hyclate, Avicel® PH 102, iron oxide yellow, crospovidone, polyvinyl pyrrolidone, colloidal silicon dioxide, and magnesium stearate were mixed to form a blend.

Controlled Release Portion
2. Doxycycline hyclate, Avicel® PH 102, Avicel® PH 200, Methocel® K100, polyvinyl pyrrolidone, and colloidal silicon dioxide were mixed to form a blend.
3. The blend of step 2 was lubricated with magnesium stearate to form a final blend.

Compression
4. The blend of step 1 was compressed, followed by the compression of the final blend of step 3 to form bilayer tablets.
5. Opadry® was dispersed in purified water to form a dispersion.
6. The tablets of step 4 were coated with the Opadry® dispersion of step 5.

Example 4

| Ingredients | Quantity (% w/w) |
|---|---|
| Doxycycline hyclate equivalent to doxycycline base 34 mg | 28.08 |
| Microcrystalline cellulose (Avicel ® PH 102) | 60.77 |
| Crospovidone | 6.00 |
| Polyvinyl pyrrolidone | 3.50 |
| Colloidal silicon dioxide | 0.50 |
| Iron oxide yellow | 0.20 |
| Magnesium stearate | 1.00 |

Manufacturing Process
1. Doxycycline hyclate, Avicel® PH 102, iron oxide yellow, crospovidone, polyvinyl pyrrolidone, colloidal silicon dioxide, and magnesium stearate were mixed to form a blend.
2. The blend of step 1 was compressed into a tablet.

Bioavailability Studies

A bioavailability study was carried out to compare the doxycycline composition prepared as per Example 1 of the present invention with Oracea® 40 mg capsules in healthy subjects under fasted and fed states. Table 1 provides the results of this study.

TABLE 1

Results of Bioavailability Study under Fasted and Fed States

| Parameter | Oracea® fasted state ($R_{fasted}$) | Example 1 fasted state ($T_{fasted}$) | Example 1 fed state ($T_{fed}$) | $T_{fasted}/T_{fed}$ | $T_{fasted}/R_{fasted}$ | $(T_{fasted} - T_{fed}/T_{fasted})*100$ |
|---|---|---|---|---|---|---|
| $C_{max}$ | 311 | 265 | 214 | 1.24 | 0.85 | 19% |
| $AUC_{0-t}$ | 6313 | 4844 | 5212 | 0.93 | 0.77 | (~−7%) |

The data in Table 1 demonstrates that the composition prepared as per the present invention has a reduced food effect wherein $C_{max}$ decreases by 19% and $AUC_{0-t}$ is almost unchanged (~−7%) as compared to the reference product Oracea® which shows a decrease in $C_{max}$ and $AUC_{0-t}$ by 45% and 22% respectively when taken along with food.

Another bioavailability study was carried out to compare the doxycycline composition prepared as per Example 2 of the present invention with Oracea® 40 mg capsules in healthy subjects under fasted and fed states. Table 2 provides the results of this study.

TABLE 2

Results of Bioavailability Study under Fasted and Fed States

| Parameter | Oracea® fasted state ($R_{fasted}$) | Example 2 fasted state ($T_{fasted}$) | Example 2 fed state ($T_{fed}$) | $T_{fed}/T_{fasted}$* | $T_{fasted}/R_{fasted}$* | $(T_{fasted} - T_{fed}/T_{fasted})*100$ |
|---|---|---|---|---|---|---|
| $C_{max}$ | 391 | 397 | 290 | 76.32 | 97.23 | (~27%) |
| $AUC_{0-t}$ | 6899 | 6522 | 6259 | 96.24 | 92.87 | (~6%) |

*based on LSGM ratio

The data in Table 2 demonstrates that the composition prepared as per the present invention has a reduced food effect wherein $C_{max}$ decreases by 27% and $AUC_{0-t}$ is almost unchanged (~−6%) as compared to the reference product Oracea®, which shows a decrease in $C_{max}$ and $AUC_{0-t}$ by 45% and 22% respectively when taken along with food.

Example 5

| Ingredients | Quantity (% w/w) |
|---|---|
| Doxycycline hyclate equivalent to doxycycline base 32 mg | 12.81 |
| Microcrystalline cellulose (Avicel® PH 102) | 62.89 |
| Microcrystalline cellulose (Avicel® PH 200) | 13.87 |
| Crospovidone | 2.91 |
| Polyvinyl pyrrolidone | 3.16 |
| Colloidal silicon dioxide | 0.49 |
| Magnesium stearate | 0.97 |
| Opadry® | 2.91 |
| Purified water | q.s. |

Manufacturing Process

1. Doxycycline hyclate, crospovidone, polyvinyl pyrrolidone, and microcrystalline cellulose were blended.
2. The blend of step 1 was lubricated with colloidal silicon dioxide and magnesium stearate.
3. The lubricated blend of step 2 was compressed into tablets.
4. The tablets of step 3 were coated with Opadry®.

Example 6

| Ingredients | Quantity (% w/w) |
|---|---|
| Doxycycline hyclate equivalent to doxycycline base 32 mg | 12.81 |
| Microcrystalline cellulose (Avicel® PH 102) | 53.18 |
| Microcrystalline cellulose (Avicel® PH 200) | 13.87 |
| Crospovidone | 2.91 |
| Polyvinyl pyrrolidone | 3.16 |
| Hydroxypropylmethyl cellulose (Methocel® K4 MCR) | 2.43 |
| Hydroxypropylmethyl cellulose (Methocel® K100 premium LVCR) | 7.28 |
| Colloidal silicon dioxide | 0.49 |
| Magnesium stearate | 0.97 |
| Opadry® | 2.91 |
| Purified water | q.s. |

Manufacturing Process

1. Doxycycline hyclate, crospovidone, polyvinyl pyrrolidone, microcrystalline cellulose, and hydroxypropylmethyl cellulose were blended.
2. The blend of step 1 was lubricated with colloidal silicon dioxide and magnesium stearate.
3. The lubricated blend of step 2 was compressed into tablets.
4. The tablets of step 3 were coated with Opadry®.

Example 7

| Ingredients | Quantity (% w/w) |
|---|---|
| Doxycycline hyclate equivalent to doxycycline base 36 mg | 14.41 |
| Microcrystalline cellulose (Avicel ® PH102) | 61.29 |
| Microcrystalline cellulose (Avicel ® PH 200) | 13.87 |
| Crospovidone | 2.91 |
| Polyvinyl pyrrolidone | 3.16 |
| Colloidal silicon dioxide | 0.49 |
| Magnesium stearate | 0.97 |
| Opadry ® | 2.91 |
| Purified water | q.s. |

Manufacturing Process
1. Doxycycline hyclate, crospovidone, polyvinyl pyrrolidone, and microcrystalline cellulose were blended.
2. The blend of step 1 was lubricated with colloidal silicon dioxide and magnesium stearate.
3. The lubricated blend of step 2 was compressed into tablets.
4. The tablets of step 3 were coated with Opadry®.

Example 8

| Ingredients | Quantity (% w/w) |
|---|---|
| Doxycycline hyclate equivalent to doxycycline base 36 mg | 14.41 |
| Microcrystalline cellulose (Avicel ® PH 102) | 51.58 |
| Microcrystalline cellulose (Avicel ® PH 200) | 13.87 |
| Crospovidone | 2.91 |
| Polyvinyl pyrrolidone | 3.16 |
| Hydroxypropylmethyl cellulose (Methocel ® K4 MCR) | 2.43 |
| Hydroxypropylmethyl cellulose (Methocel ® K100 premium LVCR) | 7.28 |
| Colloidal silicon dioxide | 0.49 |
| Magnesium stearate | 0.97 |
| Opadry ® | 2.91 |
| Purified water | q.s. |

Manufacturing Process
1. Doxycycline hyclate, crospovidone, polyvinyl pyrrolidone, microcrystalline cellulose, and hydroxypropylmethyl cellulose were blended.
2. The blend material of step 1 was lubricated with colloidal silicon dioxide and magnesium stearate.
3. The lubricated blend of step 2 was compressed into tablets.
4. The tablets of step 3 were coated with Opadry®.

Example 9

| Ingredients | Quantity (% w/w) |
|---|---|
| Doxycycline hyclate equivalent to doxycycline base 36 mg | 14.41 |
| Microcrystalline cellulose (Avicel ® PH 102) | 46.72 |
| Microcrystalline cellulose (Avicel ® PH 200) | 13.87 |
| Crospovidone | 2.91 |
| Polyvinyl pyrrolidone | 3.16 |
| Hydroxypropylmethyl cellulose (Methocel ® K4 MCR) | 7.28 |
| Hydroxypropylmethyl cellulose (Methocel ® K100 premium LVCR) | 7.28 |
| Colloidal silicon dioxide | 0.49 |
| Magnesium stearate | 0.97 |
| Opadry ® | 2.91 |
| Purified water | q.s. |

Manufacturing Process
1. Doxycycline hyclate, crospovidone, microcrystalline cellulose, hydroxypropylmethyl cellulose, and polyvinyl pyrrolidone were blended.
2. The blend material of step 1 was lubricated with colloidal silicon dioxide and magnesium stearate.
3. The lubricated blend of step 2 was compressed into tablets.
4. The tablets of step 3 were coated with Opadry®.

Example 10

| Ingredients | Quantity (% w/w) |
|---|---|
| Doxycycline hyclate equivalent to doxycycline base 36 mg | 14.41 |
| Microcrystalline cellulose (Avicel ® PH 102) | 49.15 |
| Microcrystalline cellulose (Avicel ® PH 200) | 13.87 |
| Crospovidone | 2.91 |
| Polyvinyl pyrrolidone | 3.16 |
| Hydroxypropylmethyl cellulose (Methocel ® K100 premium LVCR) | 12.14 |
| Colloidal silicon dioxide | 0.49 |
| Magnesium stearate | 0.97 |
| Opadry ® | 2.91 |
| Purified water | q.s. |

Manufacturing Process
1. Doxycycline hyclate, crospovidone, polyvinyl pyrrolidone, microcrystalline cellulose, and hydroxypropylmethyl cellulose were blended.
2. The blend material of step 1 was lubricated with colloidal silicon dioxide and magnesium stearate.
3. The lubricated blend of step 2 was compressed into tablets.
4. The tablets of step 3 were coated with Opadry®.

Example 11

| Ingredients | Quantity (% w/w) |
|---|---|
| Immediate Release Layer | |
| Doxycycline hyclate equivalent to doxycycline base 30.0 mg | 12.01 |
| Microcrystalline cellulose (Avicel ® PH102) | 31.10 |
| Crospovidone | 2.91 |
| Polyvinyl pyrrolidone | 1.70 |
| Iron oxide yellow | 0.10 |
| Colloidal silicon dioxide | 0.24 |
| Magnesium stearate | 0.49 |
| Controlled Release Layer | |
| Doxycycline hyclate equivalent to doxycycline 6.0 mg | 2.40 |
| Microcrystalline cellulose (Avicel ® PH 102) | 15.53 |
| Microcrystalline cellulose (Avicel ® PH 200) | 13.87 |
| Hydroxypropylmethyl cellulose (Methocel ® K100 premium LVCR) | 14.56 |

-continued

| Ingredients | Quantity (% w/w) |
|---|---|
| Polyvinyl pyrrolidone | 1.46 |
| Colloidal silicon dioxide | 0.24 |
| Magnesium stearate | 0.49 |
| Coating | |
| Opadry ® | 2.91 |
| Purified water | q.s. |

Manufacturing Process

Immediate Release Layer

1. Doxycycline hyclate, polyvinyl pyrrolidone, crospovidone, microcrystalline cellulose, and iron oxide yellow were blended.
2. The blend of step 1 was lubricated with colloidal silicon dioxide and magnesium stearate.

Controlled Release Layer

3. Doxycycline hyclate, hydroxypropylmethyl cellulose, polyvinyl pyrrolidone, and microcrystalline cellulose were blended.
4. The blend of step 3 was lubricated with colloidal silicon dioxide and magnesium stearate.

Compression

5. The lubricated blends of step 2 and step 4 were compressed to obtain a bilayer tablet.
6. The tablets of step 5 were coated with Opadry®.

Example 12

| Ingredients | Quantity (% w/w) |
|---|---|
| Doxycycline hyclate equivalent to doxycycline base 36 mg | 14.41 |
| Microcrystalline cellulose (Avicel ® PH 102) | 43.95 |
| Microcrystalline cellulose (Avicel ® PH 200) | 13.86 |
| Tartaric acid pellets | 5.20 |
| Crospovidone | 2.91 |
| Polyvinyl pyrrolidone | 3.16 |
| Hydroxypropylmethyl cellulose (Methocel ® K100 premium LVCR) | 12.14 |
| Colloidal silicon dioxide | 0.49 |
| Magnesium stearate | 0.97 |
| Opadry ® | 2.91 |
| Purified water | q.s. |

Manufacturing Process

1. Doxycycline hyclate, crospovidone, microcrystalline cellulose, hydroxypropylmethyl cellulose, polyvinyl pyrrolidone, and tartaric acid were blended.
2. The blend material of step 1 was lubricated with colloidal silicon dioxide and magnesium stearate.
3. The lubricated blend of step 2 was compressed into tablets.
4. The tablets of step 3 were coated with Opadry®.

Example 13

| Ingredients | Quantity (% w/w) |
|---|---|
| Doxycycline hyclate equivalent to doxycycline base 32 mg | 12.81 |
| Microcrystalline cellulose (Avicel ® PH 102) | 45.55 |
| Microcrystalline cellulose (Avicel ® PH 200) | 13.87 |

-continued

| Ingredients | Quantity (% w/w) |
|---|---|
| Tartaric acid pellets | 5.20 |
| Crospovidone | 2.91 |
| Polyvinyl pyrrolidone | 3.16 |
| Hydroxypropylmethyl cellulose (Methocel ® K100 premium LVCR) | 12.14 |
| Colloidal silicon dioxide | 0.49 |
| Magnesium stearate | 0.97 |
| Opadry ® | 2.91 |
| Purified water | q.s. |

Manufacturing Process

1. Doxycycline hyclate, crospovidone, microcrystalline cellulose, hydroxypropylmethyl cellulose, polyvinyl pyrrolidone, and tartaric acid were blended.
2. The blend material of step 1 was lubricated with colloidal silicon dioxide and magnesium stearate.
3. The lubricated blend of step 2 was compressed into tablets.
4. The tablets of step 3 were coated with Opadry®.

Pharmacokinetic Studies

Doxycycline is virtually completely absorbed after oral administration. The comparison of intravenous and oral doses of doxycycline indicated lower absorption for oral administration in the range of 73-77% (Agwuh et al., "Pharmacokinetics and pharmacodynamics of the tetracyclines including glycylcyclines," *Journal of Antimicrobial Chemotherapy*, 58(2):256-265 (2006)). This may be due to site specific absorption in the upper part of the gastrointestinal tract (GIT), i.e., in the duodenum region. The drug released beyond the duodenum remains unabsorbed.

The same is indicated from bioequivalence studies carried out on two formulations. Example 1 having an immediate-release (IR) component as 60% had shown lower bioavailability w.r.t the reference product Oracea® having an IR component as 75% as indicated from results in Table 3.

TABLE 3

Comparative pharmacokinetic data from the studies conducted under fasting condition.

| | Example 1 | Oracea ® |
|---|---|---|
| IR:CR | 60:40 | 75:25 |
| | i.e. 24:16 mg | i.e. 30:10 mg |
| $C_{max}$ (A/C) | 85.05 (75.87-95.33) | |
| $AUC_{0-t}$ (A/C) | 76.73 (68.03-86.54) | |

As doxycycline is absorbed from upper part of GIT, low bioavailability is observed in the controlled-release (CR) formulation which may be attributed to an unabsorbed portion from the CR component.

The $C_{max}$ ratio, in fact, may also be empirically derived from the calculation of the ratio of IR contribution from both formulations (i.e., 60/75=0.8).

Thus, the IR component results in complete release and absorption of drug.

Based on the above understanding, pharmacokinetic values were predicted for dosage forms containing 24-36 mg of only IR components. The bioequivalence criteria was calculated using software Phoenix 64 (WinNonlin 6.4). The results are shown in Table 4:

TABLE 4

Extrapolation of in vivo data carried out for Doxycycline Hyclate IR formulations (24-36 mg) w.r.t. RLD Oracea ® 40 mg.

| | Pharmacokinetic Parameter | |
|---|---|---|
| Formulation | $C_{max}$ T/R ratio (90% CI) | AUC T/R ratio (90% CI) |
| 24 mg | 84.68 (76.73-93.46) | 76.29 (68.40-85.09) |
| 26 mg | 91.74 (83.12-101.25) | 82.65 (74.10-92.18) |
| 28 mg | 98.79 (89.51-109.04) | 89.00 (79.80-99.27) |
| 30 mg | 105.85 (95.91-116.83) | 95.36 (85.40-106.36) |
| 32 mg | 112.91 (102.30-124.61) | 101.72 (91.20-113.46) |
| 34 mg | 119.96 (108.70-132.40) | 108.08 (96.90-120.55) |
| 36 mg | 127.02 (115.09-140.19) | 114.43 (102.60-127.64) |

(Data used is the bioequivalence study done on the Example 1 formulation and the reference product Oracea ® (40 mg) in healthy male volunteers (N = 35) in a fasting state)

The data shows that formulations containing 24 mg to 36 mg of doxycycline would be similar to existing RLD (Oracea®) in terms of pharmacokinetic parameters of $C_{max}$ and/or AUC.

We claim:

1. A once daily tablet comprising doxycycline and one or more pharmaceutically acceptable excipients, wherein the tablet exhibits a reduced food effect such that the food effect on $C_{max}$ is less than 40% compared to when the tablet is administered in a fasted state, and the food effect on $AUC_{0-t}$ is less than 20% compared to when the tablet is administered in a fasted state.

2. The once daily tablet according to claim 1, wherein the once daily tablet comprises (i) 50% to 99% of doxycycline and one or more pharmaceutically acceptable excipients as an immediate-release portion; and (ii) 1% to 50% of doxycycline, a controlled-release polymer, and one or more pharmaceutically acceptable excipients as a controlled-release portion.

3. The once daily tablet according to claim 2, wherein the immediate-release portion contains 85% of doxycycline and the controlled-release portion contains 15% of doxycycline.

4. The once daily tablet according to claim 2, wherein the immediate-release portion contains 34 mg of doxycycline and the controlled-release portion contains 6 mg of doxycycline.

5. The once daily tablet according to claim 2, wherein the immediate-release portion contains 75% of doxycycline and the controlled-release portion contains 25% of doxycycline.

6. The once daily tablet according to claim 2, wherein the immediate-release portion contains 30 mg of doxycycline and the controlled-release portion contains 10 mg of doxycycline.

7. The once daily tablet according to claim 2, wherein the immediate-release portion contains 66% of doxycycline and the controlled-release portion contains 34% of doxycycline.

8. The once daily tablet according to claim 2, wherein the immediate-release portion contains 26.4 mg of doxycycline and the controlled-release portion contains 13.6 mg of doxycycline.

9. The once daily tablet according to claim 2, wherein the immediate-release portion contains 65% of doxycycline and the controlled-release portion contains 35% of doxycycline.

10. The once daily tablet according to claim 2, wherein the immediate-release portion contains 26 mg of doxycycline and the controlled-release portion contains 14 mg of doxycycline.

11. The once daily tablet according to claim 2, wherein the immediate-release portion contains 60% of doxycycline and the controlled-release portion contains 40% of doxycycline.

12. The once daily tablet according to claim 2, wherein the immediate-release portion contains 24 mg of doxycycline and the controlled-release portion contains 16 mg of doxycycline.

13. A process for the preparation of a once daily tablet comprising doxycycline and one or more pharmaceutically acceptable excipients, wherein the tablet exhibits a reduced food effect, wherein the process comprises:
   a) preparing an immediate release portion comprising doxycycline and one or more pharmaceutically acceptable excipients;
   b) preparing a controlled release portion comprising doxycycline, a controlled-release polymer, and one or more pharmaceutically acceptable excipients; and
   c) formulating the immediate-release portion and the controlled-release portion into a tablet.

14. The process according to claim 13, wherein the tablet is a bilayered tablet.

15. The process according to claim 13, wherein the tablet comprises only an immediate-release portion.

16. The process according to claim 13, wherein the tablet comprises only a controlled-release portion.

17. A method of treating rosacea by administering to a person in need thereof a once daily tablet comprising doxycycline and one or more pharmaceutically acceptable excipients, wherein the tablet exhibits a reduced food effect such that the food effect on $C_{max}$ is less than 40% compared to when the tablet is administered in a fasted state, and the food effect on $AUC_{0-t}$ is less than 20% compared to when the tablet is administered in a fasted state.

* * * * *